United States Patent
Papanna et al.

(10) Patent No.: US 12,419,995 B2
(45) Date of Patent: Sep. 23, 2025

(54) MENINGEAL REPAIR USING HUMAN UMBILICAL CORD PATCHES

(71) Applicant: The Board of Regents, The University of Texas System, Austin, TX (US)

(72) Inventors: Ramesha Papanna, Houston, TX (US); Lovepreet K. Mann, Houston, TX (US); Stephen A. Fletcher, Houston, TX (US)

(*) Notice: Subject to any disclaimer, the term of this patent is extended or adjusted under 35 U.S.C. 154(b) by 1356 days.

(21) Appl. No.: 16/510,818

(22) Filed: Jul. 12, 2019

(65) Prior Publication Data

US 2020/0016296 A1    Jan. 16, 2020

Related U.S. Application Data

(60) Provisional application No. 62/697,371, filed on Jul. 12, 2018.

(51) Int. Cl.
   *A61L 27/38*    (2006.01)
   *A61M 13/00*    (2006.01)

(52) U.S. Cl.
   CPC ....... *A61L 27/3878* (2013.01); *A61L 27/3804* (2013.01); *A61M 13/003* (2013.01); *A61L 2400/18* (2013.01); *A61L 2430/38* (2013.01); *A61M 2240/00* (2013.01)

(58) Field of Classification Search
   None
   See application file for complete search history.

(56) References Cited

U.S. PATENT DOCUMENTS

| | | | |
|---|---|---|---|
| 9,682,044 | B2 | 6/2017 | Tseng |
| 2012/0141595 | A1 | 6/2012 | Tseng |
| 2013/0344163 | A1 | 12/2013 | Tseng |
| 2016/0106785 | A1 | 4/2016 | Tseng |
| 2016/0184368 | A1 | 6/2016 | Tseng |
| 2016/0303171 | A1 | 10/2016 | Tseng |
| 2016/0324902 | A1 | 11/2016 | Tseng |

OTHER PUBLICATIONS

Papanna, R. et al., 2016, Ultrasound Obstet Gynecol., vol. 47: pp. 168-176. Published online Oct. 2015.*
Belfort, M. et al., Apr. 2017, Obst. Gynecol., vol. 129: pp. 734-743.*
Bettina W. Paek, MD et al., "Hindbrain herniation develops in surgically created myelomeningocele but is absent after repair in fetal lambs", From the Division of Pediatric Surgery, Department of Surgery, and the Fetal Treatment Center, University of California at San Francisco. Presented at the Twentieth Annual Meeting of the Society for Maternal-Fetal Medicine, Miami Beach, Florida, Jan. 31-Feb. 5, 2000. Reprint requests: Bettina W. Paek, MD, The Fetal Treatment Center, University of California at San Francisco, San Francisco, CA 94143-0570, pp. 1-5.

* cited by examiner

*Primary Examiner* — Michael D Burkhart
(74) *Attorney, Agent, or Firm* — Thomas | Horstemeyer, LLP (57) ABSTRACT

In one embodiment, a method for performing meningeal repair includes closing an open meningeal defect with a human umbilical cord meningeal patch.

1 Claim, 5 Drawing Sheets

MENINGEAL REPAIR USING HUMAN UMBILICAL CORD PATCHES

CROSS-REFERENCE TO RELATED APPLICATION

This application claims priority to co-pending U.S. Provisional Application Ser. No. 62/697,371, filed Jul. 12, 2018, which is hereby incorporated by reference herein in its entirety.

NOTICE OF GOVERNMENT-SPONSORED RESEARCH

This invention was made with government support under Grant No. HD092754 awarded by the National Institutes of Health. The Government has certain rights in the invention.

BACKGROUND

In some circumstances, the spinal cord may not be properly surrounded by the meninges, which comprise multiple layers of tissue that protect the spinal cord. Such a defect can be the result of a disease, such as spina bifida, or the result of an injury in which a portion of the meninges is destroyed. When not properly protected by the meninges, the spinal cord is exposed and can become "tethered" to the surrounding tissues. Such tethering binds the spinal cord and, when tension is created, can result in pain, numbness, and damage to the spinal cord as well as the nerve roots.

When an individual experiences such symptoms as a consequence of spinal cord tethering, a surgical detethering procedure is typically performed in an effort to free the spinal cord and relieve the symptoms. Unfortunately, tethering often recurs after such detethering procedures and one or more follow-up detethering procedures may be required to maintain the spinal cord in an untethered state.

Due to the inconvenience, pain, costs, and risks associated with surgical detethering procedures, it can be appreciated that there is an urgent unmet clinical need for more effective means for preventing spinal cord tethering.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, there is an urgent unmet clinical need for more effective means for preventing spinal cord tethering. Disclosed herein are systems and methods designed for this purpose. More particularly, disclosed are systems and methods for repairing the meninges to prevent tethering. In some embodiments, a meningeal patch formed from the outer sheath of a human umbilical cord is implanted over a spinal defect so as to cover the spinal cord as would the meninges. Such a patch effectively prevents tethering of the spinal cord in the area of the implantation. In addition, the patch may further regenerate all or portions of the meninges, such as the arachnoid mater and the dura mater, and therefore may further improve the health and function of the spinal cord.

In the following disclosure, various specific embodiments are described. It is to be understood that those embodiments are example implementations of the disclosed inventions and that alternative embodiments are possible. Such alternative embodiments include hybrid embodiments that incorporate one or more features from different embodiments. All such embodiments are intended to fall within the scope of this disclosure.

Described in the following disclosure is a surgical graft, in the form of a meningeal patch, which can be used to close spinal defects so as to prevent tethering of the spinal cord. Cryopreserved human umbilical cord (HUC) is harvested from donated umbilical cords from healthy full-term pregnancies after delivery. The outer sheath of HUC contains heavy chain hyaluronic acid/pentraxin 3 (PTX3), which is an active component that demonstrates anti-inflammatory and anti-scarring properties. The HUC outer sheath is formed into a meningeal patch that is acellular and has anti-rejection properties. Notably, while such patches are FDA approved for ophthalmological diseases and chronic skin ulcers, they have not been approved for, or previously used for, meningeal repair. In addition to preventing spinal cord tethering, use of an HUC outer sheath as a meningeal patch may also decrease ongoing inflammation, regenerate the meninges, improve tissue healing, and achieve better clinical outcomes as compared to conventional meningeal patches, such as dura replacement matrix (DRM) patches or myofascial closure without a matrix.

Figure 1:
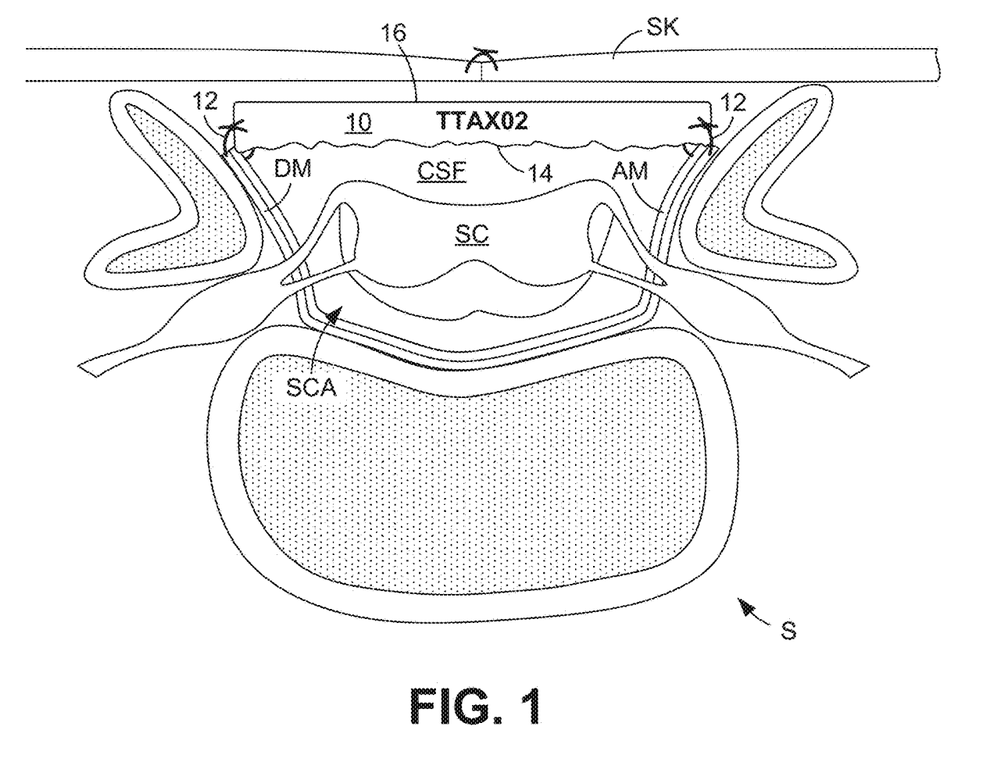
FIG. 1 is a schematic cross-sectional view of the human spine illustrating the use of a human umbilical cord (HUC) meningeal patch in a method for meningeal repair.

FIG. 1 illustrates the use of an HUC meningeal patch in a meningeal repair procedure in accordance with this disclosure. In this figure, the human spine, S, of a patient is identified in cross-section. Visible in the figure are the spinal cord, SC, which is surrounded by cerebrospinal fluid, CSF, within the spinal canal, SCA. The cerebrospinal fluid is partially enclosed by the dura mater (or layer), DM, and the arachnoid mater (or layer), AM. As indicated in FIG. 1, posterior portions of the dura layer and the arachnoid layer are absent and, therefore, the individual has an open meningeal defect. Such a defect may be the result of, for example, a congenital disease (e.g., spina bifida), an injury, or a surgical procedure. As the arachnoid layer is the central meningeal layer that contains the cerebrospinal fluid and maintains homeostasis of the surrounding neural tissue, an intact arachnoid layer is critical to preventing tethering and for normal neurological functioning.

An HUC meningeal patch 10 can be implanted to close the meningeal defect. As shown in FIG. 1, the meningeal patch 10 can be secured to the dura layer and/or the arachnoid layer with sutures 12 so as to close the meningeal defect. As described above, the HUC meningeal patch 10 can at least comprise a portion of the outer sheath of an umbilical cord of a donated placental tissue. As an example, the meningeal patch 10 can be a patch produced by TissueTech, Inc. and covered by one or more of U.S. Patent Application Nos. 2010/3344163, 2012/0141595, 2013/

0344163, 2016/0106785; 2016/0324902, 2016/0303171, 2016/0184368, and U.S. Pat. No. 9,682,044, each of which is hereby incorporated by reference in its entirety into this disclosure.

As is apparent from FIG. 1, the meningeal patch 10 includes a relatively rough inner surface 14 and a relatively smooth outer surface 16. In the illustrated embodiment, the inner surface 14 faces anteriorly inward toward the spinal cord 10, while the outer surface 164 faces posteriorly outward away from the spinal cord and toward the patient's skin, SK. Generally speaking, keratinocytes (epidermal cells) preferentially attach to the outer surface 16 of the patch 10, whereas the meningeal cells preferentially attach to the inner surface 14 of the patch. While the meningeal patch 10 is shown in FIG. 1 with its inner surface 14 facing the spinal cord and its outer surface 16 facing the skin, it is noted that, in other embodiments, the outer surface of the patch can face the spinal cord and the inner surface of the patch can face the skin.

Normally, when a conventional non-HUC meningeal patch is implanted in the manner illustrated in FIG. 1, the surgical dissection and repair that are performed can induce inflammation and scar formation, which adversely affects the underlying neural tissue. The attachment of the scar tissue to the underlying spinal cord results in spinal cord tethering, which often results in loss of function and pain that requires repetitive spinal cord surgeries to release the adhesion. When an HUC meningeal patch, such as the patch 10, is used, however, such scarring is avoided, thereby reducing the likelihood of tethering. It is also noted that, not only does the HUC meningeal patch physically cover the open meningeal defect and prevent tethering, the patch further can provide a watertight barrier and promote healing and regeneration of the meninges, including the arachnoid layer and the dura layer. In at least some cases, the HUC meningeal patch is resorbed by the body and this resorption causes the arachnoid layer and/or dura layer to grow into the patch such that the open meningeal defect is closed with the patient's own meningeal tissue. No other meningeal patch is known to possess such regenerative properties.

The above-stated assertions are partly based upon preliminary data obtained through clinical testing performed on lambs. Radiological spinal cord tethering is universally seen in all children who had in-utero or neonatal spina bifida repair causing the life-long neurological deficit and recurrent surgeries. Using a well-established ovine model for in-utero spina bifida repair, the lamb fetuses at mid-gestation were randomly treated with conventional repair (CR) using myofascial closure (n=4) versus closure using an HUC meningeal patch (or simply HUC patch) (n=4). The lambs were delivered at term and the clinical assessment for spinal cord function was performed using the Texas Spinal Cord Injury Scale (TSCIS) scale, which showed CR repair lambs with a combined hind limbs score of 13±2.3 versus 19.5±0.3 for HUC patch lambs (p=0.02; normal score in control lambs is 20).

Figure 2A:
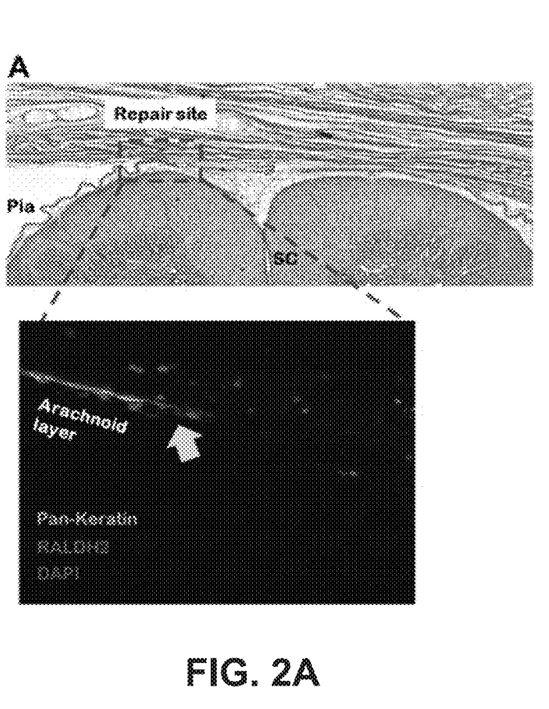
FIGS. 2A and 2B are images showing the results of conventional meningeal repair and HUC meningeal repair, respectively.
Figure 2B:
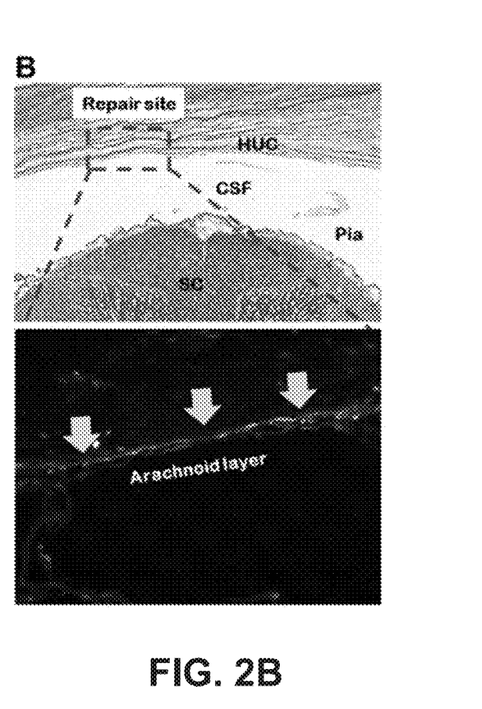

Regarding histology, there was significantly reduced tethering noted in the HUC patch repair lambs (12.8%±1.9%) as compared to conventional repair lambs (55%±12%) of the posterior surface to repair site, as illustrated in FIGS. 2A and 2B. The arachnoid layer was regenerated into the HUC on the histology in the HUC patch lambs and none in the CR lambs, as was confirmed using specific immunofluorescence markers Pan-keratin, retinaldehyde dehydrogenase 2 (RALDH-2), and Collagen-VI. These results suggest that HUC patches may regenerate the arachnoid and dura layers and prevent tethering in an adults with spinal cord injuries.

Figure 3:
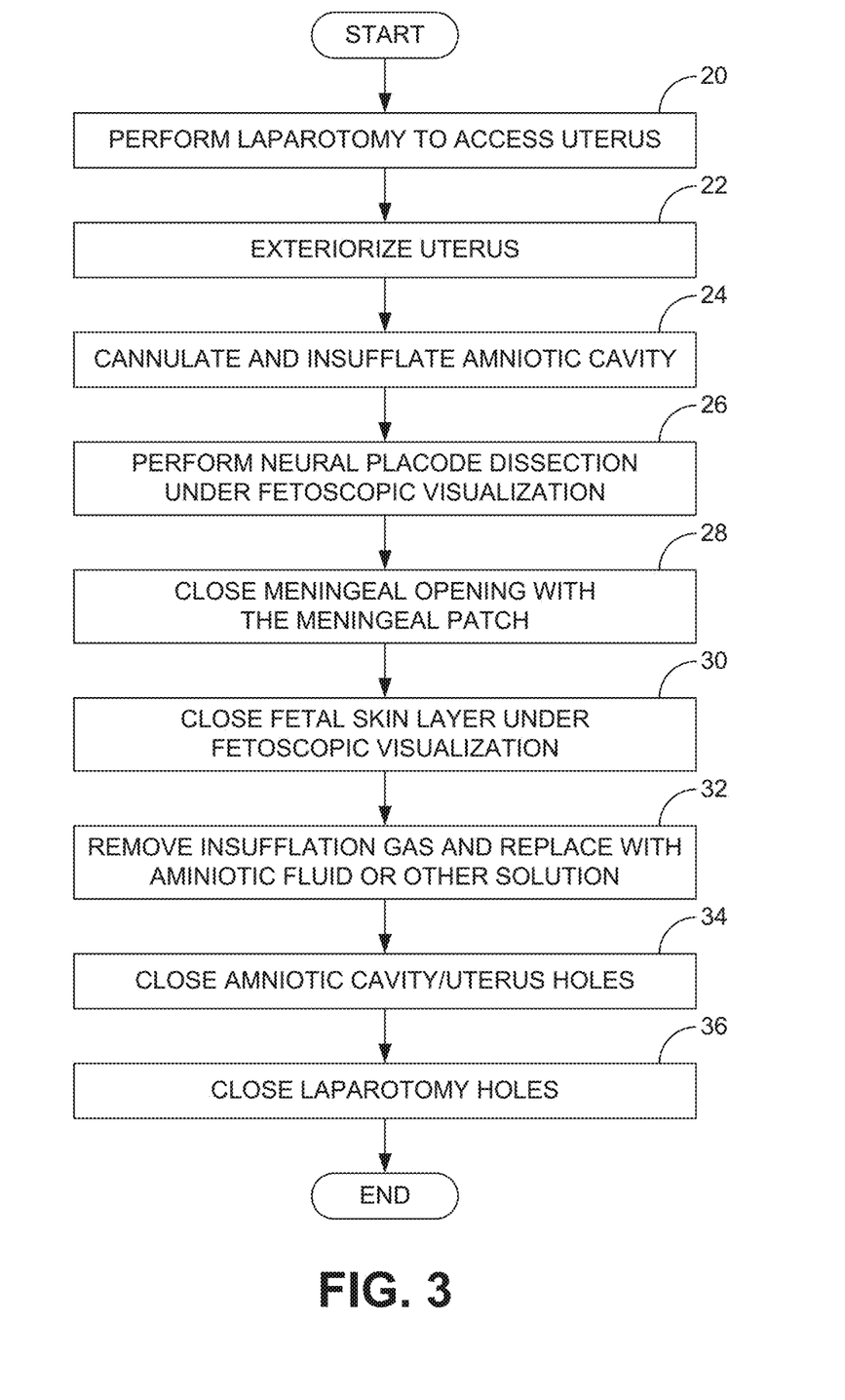
FIG. 3 is a flow diagram of an embodiment of a minimally invasive in-utero meningeal repair procedure.

As can be appreciated from the above discussion, one potential application for the HUC patch and the meningeal repair it provides is for repairing spina bifida defects. In some embodiments, a minimally invasive in-utero meningeal repair procedure can be performed on a fetus of a pregnant mother using the HUC patch. As noted above, use of the meningeal patch improves outcomes for patients. Performing meningeal repair via a minimally invasive laparoscopic procedure provides additional advantages. Specifically, a minimally invasive laparoscopic procedure is faster and less traumatic for the mother than open surgery. Furthermore, a minimally invasive laparoscopic procedure enables the mother to give birth vaginally as opposed to via Cesarean section (C-section), which is typically the case when open surgery is performed to perform a spina bifida repair. FIG. 3 is a flow diagram that illustrates an example method for performing minimally invasive in-utero meningeal repair.

Beginning with block 20 of FIG. 3, a laparotomy is performed on the pregnant mother to access the uterus. Next, with reference to block 22, the uterus is exteriorized in order to obtain better access to both the uterus and the fetus. The fetus can be further be positioned using external cephalic version (ECV). Once the uterus and/or fetus has been positioned in the desired location and orientation, the amniotic cavity can be cannulated and insufflated, as indicated in block 24. In some embodiments, the amniotic cavity is accessed with three separate cannulas and insufflated with heated and humidified carbon dioxide ($CO_2$).

At this point, neural placode dissection can be performed under fetoscopic visualization, as indicated in block 26. Next, with reference to block 28, the meningeal defect is closed using the meningeal patch in the manner described above with reference to FIG. 1. Once the meningeal patch has been secured in place, for example with sutures, the fetal skin layer can be closed under fetoscopic visualization (block 30), the insufflation gas can be removed and replaced with amniotic fluid or another suitable solution (block 32), the amniotic cavity and uterine holes can be closed (block 34), and the laparotomy holes can be closed (block 36).

A study was conducted to evaluate the aforementioned minimally invasive in-utero meningeal repair procedure. Two patches were tested in a retinoic acid-induced spina bifida defect rat model system. The patches included cryopreserved HUC patch and an acellular dermal matrix (ADM) patch. The HUC was an acellular matrix prepared from donated human placentas collected from full-term C-section deliveries. The HUC was then cryopreserved to create a patch that is compliant with the American Association of Tissue Banks and the current Good Tissue Practices, as set forth by the Federal Food and Drug Administration (FDA). After removal of the umbilical cord's vessels, it was flattened to generate various sized patches. The outer surface of the patch (which faced the amniotic cavity) had a smooth epithelial layer, and the inner surface of the patch (which faced the umbilical vessels) had a rough mesenchymal surface that contained Wharton's jelly. Wharton's jelly reduces inflammation and scar formation, and promotes the regeneration of undifferentiated native cells.

The inventors previously determined through experimentation that the HUC patch provides a watertight barrier and prevents hindbrain herniation (HH) in a surgical in-utero spina bifida repair sheep model. In other studies using the same spina bifida defect model system in a rat, the inventors established that the HUC patch is superior to biocellulose film for the suppression of inflammation and the promotion of undifferentiated cell infiltration. Under an FDA Expanded Access protocol, two human fetuses' large skin spina bifida defects that could not be closed primarily were repaired in-utero with the HUC patch. Both pregnancies were uncomplicated with a full-term delivery. The repair sites of both neonates were intact and were clinically noted to have HH reversal, normal bladder control, and normal lower limb function. Magnetic resonance imaging (MRI) of the neonatal spines showed little to no scar formation between the spinal cord and the repair site.

The ADM patch (Alloderm, LifeCell Corporation, Branchburg, N.J.) was prepared from donated human cadaveric skin. As with the HUC patch, the ADM patch has two distinct sides: a dermal side and a basement membrane side. The ADM patch has traditionally been used for spina bifida defect repair when primary skin closure is not possible. However, the clinical outcomes of these patients and the polarity of the ADM patch has not been well studied. In a surgical sheep model of spina bifida, the ADM patch was shown to reduce HH but resulted in significant tethering of the spinal cord at the repair site.

The primary objective of the new study was to compare the HUC patch to the ADM patch for their anti-inflammatory and regenerative cellular responses in a retinoic acid-induced rat spina bifida model. The secondary objective was to evaluate the polarity of HUC and ADM patches for their abilities to regenerate primary human meningeal cells in-vitro.

Once the study protocol was approved by the Animal Welfare Committee (AWC-14-0069), the study was performed at the UT Health University of Texas McGovern Medical School at Houston. All animal care complied with the Guide for the Care and Use of Laboratory Animals.

The generation of the spina bifida defects were based on animal models of pregnant Sprague Dawley rats (210-300 g) that were time-dated to gestational age day 6 (GD6). The rats were individually housed at the Center for Laboratory and Animal Medicine with a 12:12 dark:light cycle at 22° C., were fed a regular diet, and were checked on daily for their well-being. On GD10, a 40 mg/kg dose of all-trans retinoic acid (ATRA; Sigma-Aldrich, St. Louis, Mo.) in 2 ml of olive oil was prepared within 30 minutes of administration. Pregnant rats, otherwise known as dams, were manually restrained and the ATRA solution administered by oral gavage at 19:00 hr.

Survival surgery was performed on GD20. Briefly, isoflurane gas-anesthetized dams were positioned in the supine position. Preoperative analgesia consisting of 0.25% bupivacaine and 0.05 mg/kg buprenorphine was then administered. Under sterile conditions, a midline laparotomy was performed and the uterine horns exteriorized. Trans-illumination identified pups with spina bifida defects. Two pups per dam were selected and randomly assigned to a repair arm of either an HUC or an ADM patch. A hysterotomy exposed the site of the defect and a circumferential incision was made to create a fresh wound between the skin edge and the meningeal layers. The HUC or ADM patches were secured to the skin edges adjacent to the neural placode (NP) using three to four 6-0 Monocryl sutures (Ethicon Inc., Somerville, N.J.). The HUC patches were provided by TissueTech, Inc. and the ADM patches were purchased (Biohorizons, Birmingham, Ala.).

For the spina bifida defects assigned to HUC repair, care was taken to orient the patch so that the mesenchymal side faced the NP and that the epithelial side faced the amniotic cavity. For the ADM patch, the dermal side faced the NP per the manufacturer's instructions. After patch placement, 1-2 ml of sterile saline was instilled into the uterine cavity to replace amniotic fluid loss, followed by closure of the hysterotomy incision. The abdomen was then closed, and the animal was allowed to recover from anesthesia.

On GD 22, dams were anesthetized using isoflurane 48-52 hours after repair. A midline laparotomy was performed and fetus viability was assessed by noting their fetal movements and responses to touch. Following a hysterectomy, the intact uterus was placed on ice to induce hypothermic fetal anesthesia. Following dam euthanization by exsanguination, intact amniotic sacs were individually removed from the uterus and placed in a finger of a sterile examination glove, followed by submersion in a cold saline slush until fetal immobilization. Pups were euthanized by decapitation. The repair sites on the pups, including the patches, were then excised with 5 mm margins for standard histological processing. Mid-level cross-sections of the repair sites were paraffin-embedded.

Next, tissue specimens were sectioned (4 µm), mounted, and stained with hematoxylin and eosin (H&E) or Masson's trichrome to evaluate cellular tropism to the patches. Immunofluorescence (IF) was performed to assess specific cellular responses at the repair sites. Briefly, unstained slides were deparaffinized and rehydrated in graded alcohols, and antigen retrieval was performed using a 10 mM sodium citrate buffer (pH=6). Tissue sections were incubated with primary antibodies overnight at 4° C. for antigen detection. To determine the in-vivo regenerative properties of epithelial cells in dermal elements, an anti-cytokeratin-5/6 antibody (Cyt-5/6; 1:50; MAB1620, EMD Millipore, Temecula, Calif.) was used. For in-vitro keratinocyte co-culture experiments with the patches, dermal elements were assessed using an anti-cytokeratin-1 (CK-1; 1:100; ab83664, Abcam, Cambridge, Mass.) antibody. To assess meningeal fibroblast tropism to the patches, anti-chondroitin sulfate-56 (CS-56; 1:50; C-8035, Sigma-Aldrich, St. Louis, Mo.) and anti-retinaldehyde dehydrogenase type-2 (RALDH2; 1:100; ABN420, Millipore, Temecula, Calif.) antibodies were used. Fibronectin (FN; 1:100; ThermoFisher Scientific, Carlsbad, Calif.) assessed the extracellular matrix component of the patches.

To determine inflammatory responses surrounding the patches, a neutrophil-specific anti-myeloperoxidase antibody (MPO; 1:300; RB-373-A, Thermo Scientific, Rockford, Ill.) and a macrophage-specific anti-F4/80 antibody (F4/80; 1:25; 14-4801, eBioscience, Santa Clara, Calif.) were used. To evaluate astrocytes encompassing the patches, an anti-glial fibrillary acidic protein antibody (GFAP; 1:300; AB5804, EMD Millipore, Temecula, Calif.) was used. Biotinylated Alexa Fluor 488 goat anti-mouse or an Alexa Fluor 555 goat anti-rabbit were used as secondary antibodies (Invitrogen; 1:1000; Carlsbad, Calif.). 4',6-diamidino-2-phenylindole (DAPI; ThermoFisher Scientific, Carlsbad, Calif.) counterstained nuclei. Sections where the primary antibody was omitted or replaced by non-immune IgG served as negative controls. Terminal deoxynucleotidyl transferase dUTP nick end labeling (TUNEL) staining detected late stage apoptosis according to the manufacturer's instructions (Abcam, Cambridge, Mass.). Six high powered (40× magnification) digital images of each section was obtained using a Zeiss Axio Imager A2 microscope (Carl Zeiss, San Diego, Calif.), where three images were taken of outer and inner patch surfaces. Using Z-Pro software (Carl Zeiss, San Diego, Calif.), the total number of specific cell types were quantified. Counts were obtained blindly by two independent observers.

To evaluate the surface polarities of the HUC and ADM patches, in-vitro experiments were performed using primary human meningeal cells (ScienCell Research Laboratories, Carlsbad, Calif.) or human neonatal keratinocyte cells (Millipore, Burlington, Mass.). The aforementioned cells were seeded at $1\times10^5$ cells per well in 6-well plates and cultured in either a meningeal cell growth medium with a 1× meningeal cell growth supplement (ScienCell, Carlsbad, Calif.) or in serum-free EpiGro human keratinocyte culture media (Millipore, Burlington, Mass.), respectively. Media were supplemented with 10% heat-inactivated fetal bovine serum (Life Technologies, Carlsbad, Calif.) and 100 IU/ml penicillin 100 µg/ml streptomycin (Thermofisher Scientific, Carlsbad, Calif.). Media was replaced 48 hours after seeding and 10 mm×5 mm HUC or ADM patches were placed on top of confluent monolayers. The HUC and ADM patches were placed in separate wells and each patch was tested on both sides. After 21 day co-culture experiments with the primary human meningeal cells, or after 14 day co-culture experiments with human neonatal keratinocyte cells, patches were fixed in 4% paraformaldehyde and processed for further analysis as detailed above.

Results were reported as either mean ±SEM or median with range, as appropriate. Data were compared using an unpaired t-test or a Mann-Whitney U test. A p-value of <0.05 was considered significant. Statistical analyses were performed using GraphPad Prism 6 software (GraphPad Software Inc., La Jolla, Calif.).

A total of 18 dams underwent the spina bifida defect repair surgery. The HUC patch was used to repair the spina bifida defect in 11 pups, whereas the ADM patch was used to repair defects in 10 pups. Patch integrities, defined as patches covering the lesion at the time of harvest, were similar between the HUC and ADM repair groups (91% and 90%, respectively; p=0.9). No significant differences were found in survival rates between pups receiving the HUC patch versus in the ADM patch group [8/11 (73%) and 7/10 (70%), respectively; p=0.9; data not shown]. Notably, the surviving pups had an intact patch covering the lesion. H&E and Masson's trichrome staining of the resected repair sites with the different patches revealed cellular migration enclosing both HUC and ADM patches. Under higher magnification, the total cell counts infiltrating the patches at the repair site were determined by DAPI staining were found to be similar.

The phenotypic assessments of cell infiltration were performed on both surfaces of the patches. IF evaluation of the presence of epithelial cells (Cyt 5/6) revealed their preferential localization to the outer surface, and not the inner surface, of HUC patches. In contrast, epithelial cells were found on the outer and inner surfaces of ADM patches. Significant differences in epithelial cell localization was noted on the outer surfaces of the respective patches, but not on their inner surfaces. Meningeal cells (co-localization of anti-CS-56 and anti-RALDH2 antibodies) infiltrated the inner surfaces of the HUC patches and were absent from the outer surfaces. In contrast, meningeal cells localized to both inner and outer surfaces of ADM patches. No statistical differences were found in the preferential inner surface localization of meningeal cells between the two patch types. However, meningeal cells unpreferentially localized to ADM's outer surfaces. GFAP-positive cells were not seen on the outer surface of the HUC patches but were identified in the ADM patches, which was not statistically significant. Increased numbers of GFAP-expressing astrocytes localized to the inner surface of ADM patches compared to those of the HUC patches and this difference was statistically significant. Cumulatively, these findings suggest that there is a cell mobilization preference towards natural surfaces of the HUC patch compared to the ADM patch.

Both the HUC and ADM patches, and their surrounding exudates, were compared for inflammatory cell recruitment. Neutrophils (MPO-positive staining) in the patches and their surrounding exudates were elevated in ADM patches compared to the HUC patch group. Macrophage (F4/80-positive staining) infiltration was found to be similar between the two different patches). Apoptosis tended to increase in the exudates surrounding the ADM patch compared to the HUC patch, however no differences were noted on the surface of the patches.

To evaluate preferential cellular tropism of human keratinocytes and of human meningeal cells to surfaces of HUC and ADM patches, the inner and outer sides of both patches were co-cultured independently with each of the aforementioned cells in-vitro. The number of keratinocytes that migrated to either side of the HUC and ADM patches were counted by means of nuclei quantification of H&E stained sections and confirmed by IF with anti-CK-1. A significantly enhanced number of keratinocytes migrating to the epithelial side of the HUC patch was observed as compared to its mesenchymal side (p=0.013), and no tropism of keratinocytes to either side of the ADM patch.

Meningeal cell numbers were initially quantified on both sides of each patch type by DAPI staining. There were increased numbers of meningeal cells (anti-CS-56 for meningeal cell detection and anti-FN staining for patch scaffolding detection) on the mesenchymal side of the HUC patch compared to the basal membrane side of the ADM patch in 21-day co-cultures. Only a scant number of meningeal cells were present on the dermal and basal membrane surfaces of the ADM patch on day 21. Human meningeal cells infiltrated the epithelial surface of the HUC patch to a higher degree than the dermal side of the ADM patch in culture. Overall there was a preferential tropism of meningeal cells to the mesenchymal side of the HUC patch compared with its epithelial side.

Figure 4A:
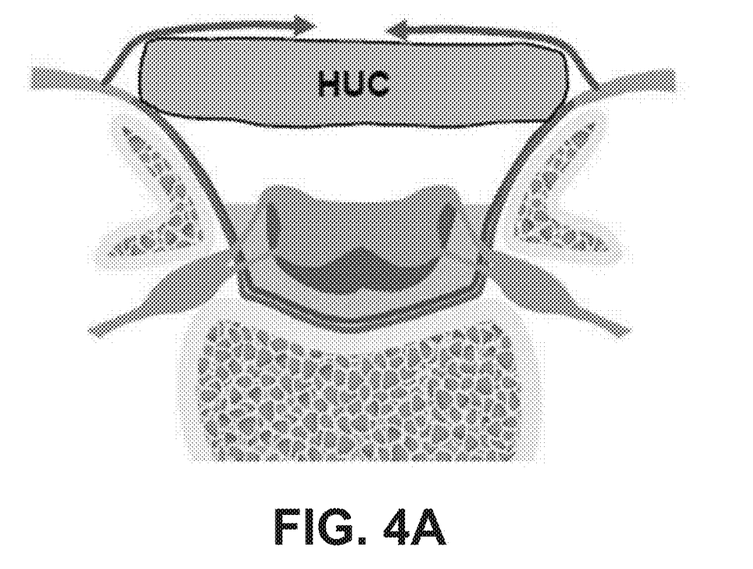
FIG. 4A is a diagram illustrating preferential migration of epidermal cells to the HUC patch.
Figure 4B:
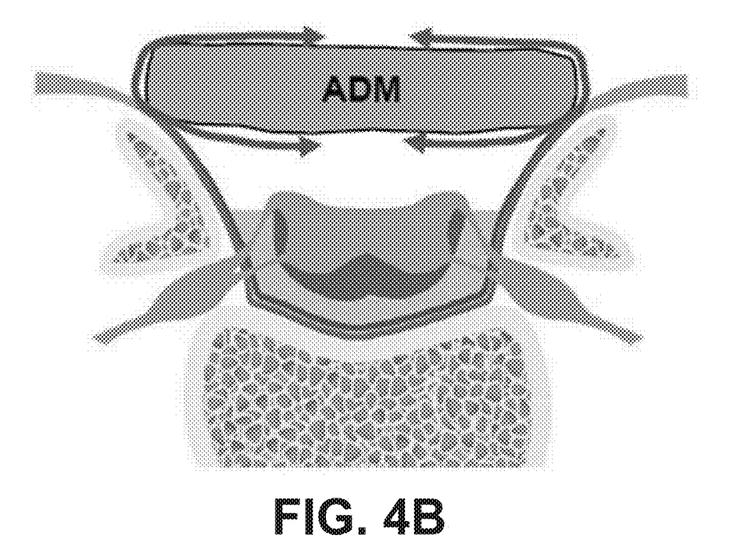
FIG. 4B is a diagram illustrating non-preferential migration of epidermal cells to the ADM patch.
Figure 4C:
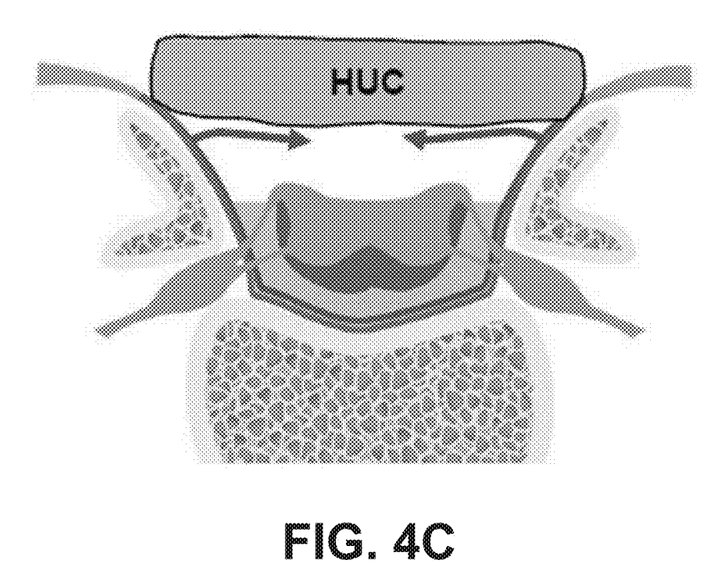
FIG. 4C is a diagram illustrating preferential localization of meningeal cells to the inner surface of the HUC patch.
Figure 4D:
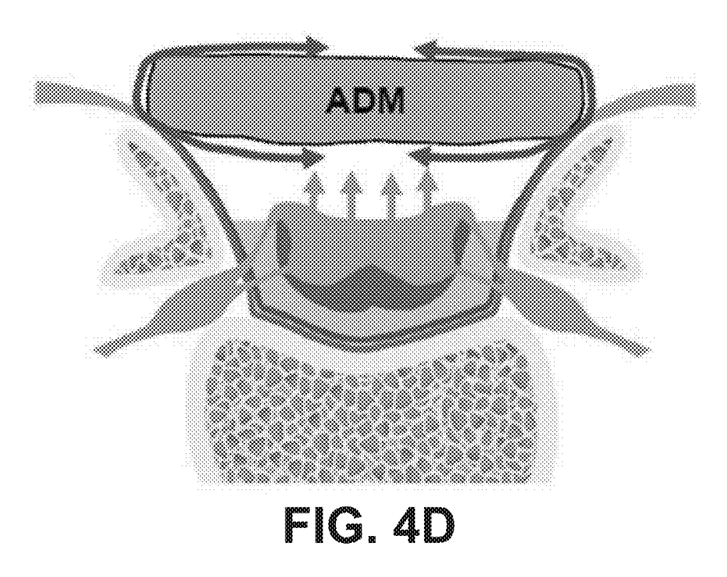
FIG. 4D is a diagram illustrating non-preferential tropism of meningeal and GFAP cells of the ADM patch.

Cumulatively, the in-vivo data suggests that the HUC patch preferentially accumulates meningeal cells on its mesenchymal surface when compared to the ADM patch at repair sites, with similar findings for the tropism of epithelial cells to the outer surface of the HUC patch at the repair sites (FIG. 4A-D). Finally, it was found that both epithelial and meningeal cells did not exhibit any tropic preference to either side of the ADM patch (FIGS. 4B, 4D).

In summary then, the HUC patch allows for regenerative repair after in-utero repair of spina bifida defects in the rat model with lower levels of acute inflammation when compared to the ADM patch. The study suggests that the HUC patch exhibits a superior ability to promote organized cellular infiltration at the repair site, together with an improved suppression of inflammation when compared to ADM material. Unlike the ADM patch, the HUC patch promotes meningeal cell tropism to the mesenchymal side of the patch, thereby protecting the spinal cord. The preferential organization of cellular infiltration into and surrounding the patches may be related to the inherent properties of their surfaces. In-vivo, the epithelial side of the umbilical cord faces the amniotic fluid, and the mesenchymal side faces the blood vessels.

The meningeal layers play an important role in the homeostasis and protection of the spinal cord. Infiltration of meningeal cells to the mesenchymal side of the HUC patch opens up the possibility for its use as a meningeal patch. This unique property could impact other neurosurgical procedures geared at reducing spinal cord tethering and improving upon spinal cord anatomy and function. Regeneration of the meningeal layers after spina bifida repair plays a role in the improvement of spinal cord function together with decreased spinal cord tethering. It is surmised that ADM patch astrocyte attachment may also have implications for the etiology of spinal cord tethering. Collectively, the study offers insight into the therapeutic potential of HUC patches, specifically for the regeneration of congenital anatomical defects such as spina bifida, and the possible benefits for other birth defects such as congenital diaphragmatic hernia and gastroschisis.

While the above disclosure has been focused on open meningeal defects of the spinal cord, it is noted that the disclosed HUC patch can be used to close open meningeal defects of the brain as well.

The invention claimed is:

1. A method for performing meningeal repair, the method comprising:
   closing an open meningeal defect with a human umbilical cord meningeal patch by covering the open meningeal defect with the human umbilical cord meningeal patch and suturing the human umbilical cord meningeal patch to the meninges, wherein the human umbilical cord meningeal patch comprises an outer sheath of a cryopreserved human umbilical cord.

* * * * *